(12) United States Patent
Kozlow et al.

(10) Patent No.: US 9,709,544 B2
(45) Date of Patent: Jul. 18, 2017

(54) SOLID STATE GAS DETECTION SENSOR DIAGNOSTIC

(71) Applicant: Rosemount Analytical Inc., Calgary (CA)

(72) Inventors: Henryk Kozlow, Calgary (CA); Lucjan Antoni Oleszczuk, Calgary (CA)

(73) Assignee: Rosemount Analytical Inc., Calgary, AB (CA)

( * ) Notice: Subject to any disclaimer, the term of this patent is extended or adjusted under 35 U.S.C. 154(b) by 120 days.

(21) Appl. No.: 14/621,706

(22) Filed: Feb. 13, 2015

(65) Prior Publication Data

US 2015/0233880 A1    Aug. 20, 2015

Related U.S. Application Data

(60) Provisional application No. 61/940,002, filed on Feb. 14, 2014.

(51) Int. Cl.
*G01N 33/00* (2006.01)

(52) U.S. Cl.
CPC ....... *G01N 33/007* (2013.01); *G01N 33/0006* (2013.01)

(58) Field of Classification Search
CPC  G01L 27/007; G01N 33/005; G01N 33/0044; G01N 33/0037; G01N 33/0042; G01N 33/0054; G01N 1/2214; G01N 2030/143; G01N 27/4045
See application file for complete search history.

(56) References Cited

U.S. PATENT DOCUMENTS 4,502,321 A * 3/1985 Zuckerman ........... G01N 27/12
                                                    73/25.03
4,847,783 A    7/1989 Grace et al.
(Continued)

FOREIGN PATENT DOCUMENTS

AT    EP 2279399 B1 *  1/2013  ........... G01L 27/007
JP         06331583 A  * 12/1994
JP         10054285 A  *  2/1998

OTHER PUBLICATIONS

"ECO-SENSE Electrochemical H2S Product Data Sheet", Emerson Process Management, Jul. 2012.*
(Continued)

*Primary Examiner* — David A Rogers
(74) *Attorney, Agent, or Firm* — Christopher R. Christenson; Kelly, Holt & Christenson PLLC

(57) ABSTRACT

A metal oxide semiconductor-based toxic gas detector is provided. The metal oxide semiconductor-based detector includes a metal oxide semiconductor-based gas sensor that has an electrical characteristic that varies with concentration of a toxic gas. Measurement circuitry is coupled to the metal oxide semiconductor-based gas sensor and is configured to measure the electrical characteristic and provide a digital indication of the measured electrical characteristic. A controller is coupled to the measurement circuitry and is configured to provide a toxic gas output based on the digital indication. The controller is also configured to provide a diagnostic output relative to the metal oxide semiconductor-based sensor based on fluctuations of the measured electrical characteristic over time.

17 Claims, 4 Drawing Sheets

(56) References Cited

U.S. PATENT DOCUMENTS

| | | | | |
|---|---|---|---|---|
| 5,670,949 | A * | 9/1997 | Kirby | G01N 27/12 340/632 |
| 5,841,021 | A * | 11/1998 | De Castro | G01N 27/4162 204/424 |
| 5,901,691 | A * | 5/1999 | Katoh | F02D 41/1495 123/688 |
| 5,932,079 | A * | 8/1999 | Haupt | G01N 27/4045 204/412 |
| 6,935,155 | B2 | 8/2005 | Yasui et al. | |
| 7,208,327 | B2 * | 4/2007 | Gstrein | G01N 27/129 438/10 |
| 7,210,455 | B2 * | 5/2007 | Visser | F02P 5/1502 123/1 A |
| 7,240,535 | B2 * | 7/2007 | Wohltjen | G01N 1/2214 73/23.42 |
| 7,603,980 | B2 * | 10/2009 | Watanabe | F02D 9/02 123/396 |
| 7,947,226 | B2 * | 5/2011 | Takahashi | G01N 27/16 422/83 |
| 8,063,631 | B2 * | 11/2011 | Fermon | G01N 27/9046 324/235 |
| 8,290,721 | B2 | 10/2012 | Wehrs et al. | |
| 2002/0092344 | A1 * | 7/2002 | Ward | G01L 3/26 73/114.26 |
| 2002/0180609 | A1 * | 12/2002 | Ding | G01N 27/4035 340/633 |
| 2007/0027609 | A1 * | 2/2007 | Watanabe | F02D 9/02 701/114 |
| 2007/0292957 | A1 * | 12/2007 | Chua | G01N 15/0826 436/5 |
| 2009/0249859 | A1 * | 10/2009 | Takahashi | G01N 27/16 73/23.31 |
| 2010/0201989 | A1 * | 8/2010 | Zhou | G01N 21/3504 356/437 |
| 2012/0161796 | A1 * | 6/2012 | Smith | G01N 27/125 324/693 |
| 2012/0185179 | A1 * | 7/2012 | Zhou | G01N 21/3504 702/24 |
| 2014/0366610 | A1 * | 12/2014 | Rodriguez | G01N 33/497 73/23.3 |

OTHER PUBLICATIONS

Pandey et al., "A review of sensor-based methods for monitoring hydrogen sulfide", TrAC Trends in Analytical Chemistry, Feb. 2012.*

Machine translation of JP 6-331583 A which originally published on Dec. 2, 1994.*

International Search Report and Written Opinion for International Application No. PCT/US2015/015774, date of mailing: May 29, 2015, date of filing: Feb. 13, 2015, 13 pages.

"Net Safety Monitoring Inc., Millennium II Toxic Gas Sensor", H2S Solid State Sensor User Manual, Model: ST321X-100-ASSY, Aug. 2010, Net Safety Monitoring Inc., 24 pages.

International Preliminary Report on Patentability for International Patent Application No. PCT/US2015/015774, date of mailing: Aug. 25, 2016, date of filing: Feb. 13, 2015, 10 pages.

First Office Action for Chinese Patent Application No. 201580000169.X, dated Aug. 1, 2016, 13 pages.

Second Office Action for Chinese Application 201580000169.X, dated Mar. 28, 2017, 14 pages including English translation.

* cited by examiner

SOLID STATE GAS DETECTION SENSOR DIAGNOSTIC

CROSS-REFERENCE TO RELATED APPLICATION

The present application is based on and claims the benefit of U.S. Provisional Patent Application Ser. No. 61/940,002, filed Feb. 14, 2014, the content of which is hereby incorporated in its entirety.

BACKGROUND

Toxic gas, such as hydrogen sulfide gas, can be deadly even at low concentrations. Generally, when one is exposed to such a toxic gas, it is imperative to seek medical attention relatively quickly. Accordingly, in many industrial situations, it is very important to be able to detect toxic gas in very low concentrations as soon as possible when a leak occurs, even in the most challenging and remote conditions. Moreover, it is important that a toxic gas sensor be ready to perform its function even when the occurrence of a toxic gas leak is extremely rare.

Health and safety standards in many countries have been slowly decreasing the acceptable exposure levels as sensor response times and overall stability of sensing elements have improved. For example, in the United States, the Occupational Safety and Health Administration (OSHA) provides an acceptable concentration limit for exposure to hydrogen sulfide at 20 parts per million (ppm) for an 8-hour period, with the maximum peak exposure at 50 ppm for 10 minutes.

An important goal of any fixed-location toxic gas detector is to safeguard workers and the public by warning of the presence of hazardous levels of such toxic gas in the proximity of the sensor. Electrochemical and Metal Oxide Semiconductor (MOS) cells have, for many years, been field-proven toxic gas sensing technologies. MOS-based sensors have a long life compared to electrochemical sensors and continue to operate in wide ranging temperatures, particularly high temperatures, as well as in extremely dry conditions.

In some implementations, a toxic gas sensor may be constructed as a sandwich of a platinum heater element, an insulation medium and gas-sensitive resistive film. In other implementations, a toxic gas sensor, such as a hydrogen sulfide sensor, may be constructed as a bead having a heater disposed therein and a lead wire running through the bead. The bead is formed of a gas-sensitive semiconductor. This gas-sensitive material will employ traditional metal oxide semiconductor materials or metal oxide semiconductor materials that are enhanced at the nano-level to dramatically improve performance. During operation, when a toxic gas comes into contact with the gas-sensitive material, there is a measurable change in the electrical conductivity of the sensor. These changes are typically amplified using electronics in a detector device.

This type of sensor typically utilizes the polycrystalline structure of the sensing material (semiconductor metal oxide) and the existence of the negatively charged surface oxygen species, which controls the height of the Schottky barrier and the electrical resistance of the material. When the sensor is exposed to certain reducing gases, the surface oxygen will be consumed, reducing the Schottky barrier, and the resistance, which is the sensing signal.

In order to ensure that a metal oxide semiconductor toxic gas sensor is able to provide a viable signal, it is important for diagnostics to be able to test, or otherwise determine if the sensor has become damaged, or otherwise deteriorated.

SUMMARY

A metal oxide semiconductor-based toxic gas detector is provided. The metal oxide semiconductor-based detector includes a metal oxide semiconductor-based gas sensor that has an electrical characteristic that varies with concentration of a toxic gas. Measurement circuitry is coupled to the metal oxide semiconductor-based gas sensor and is configured to measure the electrical characteristic and provide a digital indication of the measured electrical characteristic. A controller is coupled to the measurement circuitry and is configured to provide a toxic gas output based on the digital indication. The controller is also configured to provide a diagnostic output relative to the metal oxide semiconductor-based sensor based on fluctuations of the measured electrical characteristic over time.

DETAILED DESCRIPTION

As set forth above, diagnostics of toxic gas sensors is an important aspect of ensuring that the toxic gas sensor is operating effectively and will be able to provide a trustworthy signal in the event that toxic gas becomes present. Utilization of toxic gas sensors based on semiconductor metal oxide sensing technology in safety applications requires various diagnostics to detect failure modes in the sensor. For such safety applications, it is necessary to detect all failure modes that the sensor may be subjected to, such as a short of the sensor element and an open sensor element.

Embodiments of the present invention generally detect a more subtle failure mode in solid state metal oxide semiconductor toxic gas sensors. Specifically, the failure mode is known as a stale sensor. When this failure mode occurs, the sensor reading will not effectively indicate a toxic gas concentration. However, the sensor will continue to indicate an actual resistance. Thus, sensor diagnostics based on detecting a short or an open circuit will not detect a stale failure. Instead, embodiments of the present invention generally leverage an aspect of a metal oxide semiconductor toxic gas sensor signal in order to detect a stale failure. Specifically, when a metal oxide semiconductor toxic gas sensor is operating correctly, the sensor resistance will have a natural variation or fluctuation. Generally, sensor electronics have subjected the sensor input signal to a low pass filter in order to remove these variations. Thus, the resistance of the sensor is processed or otherwise characterized in order to remove the fluctuations prior to providing a toxic gas sensor output. However, in accordance of embodiments of the present invention, as set forth below, these variations are specifically measured and used to provide a diagnostic indication relative to the metal oxide semiconductor toxic gas sensor.

Figure 1:
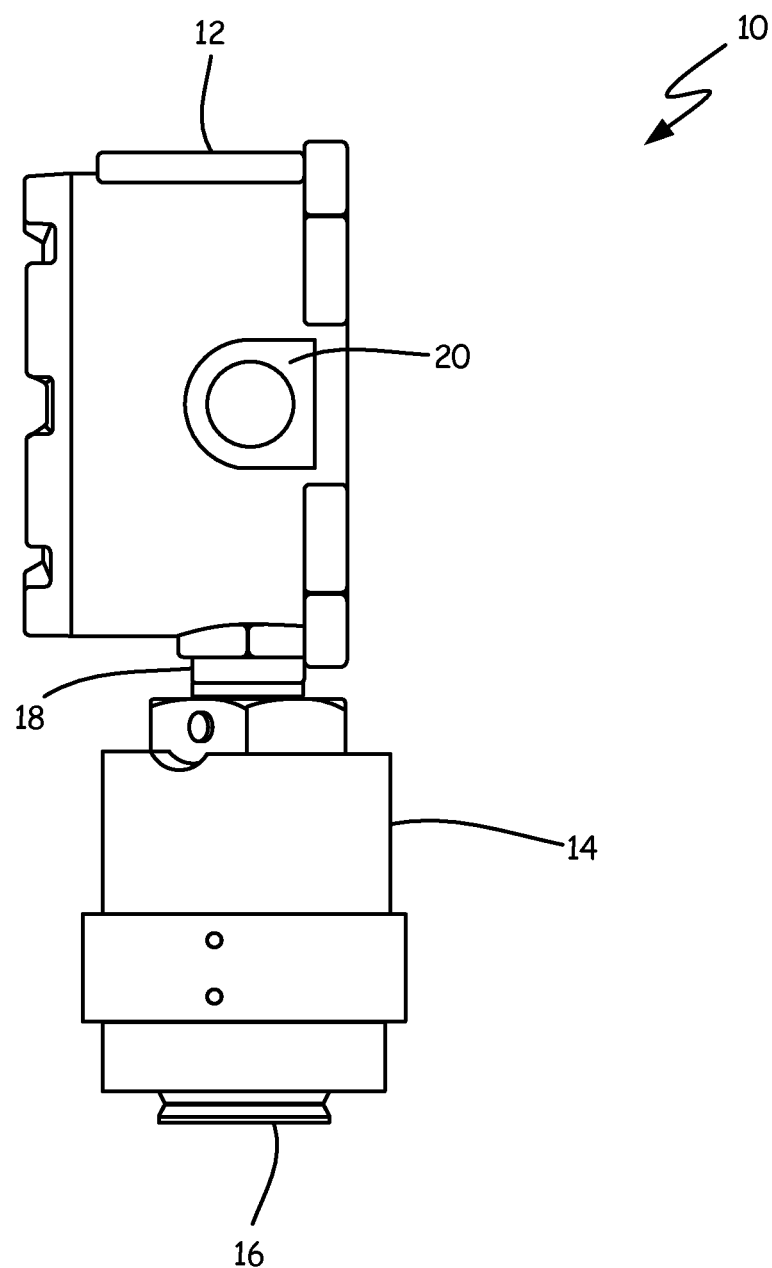
FIG. 1 is a diagrammatic view of a metal oxide semiconductor toxic gas detector with which embodiments of the present invention are particularly useful.

FIG. 1 is a diagrammatic view of a metal oxide semiconductor toxic gas detector with which embodiments of the present invention are particularly useful. Detector 10 includes electronics enclosure 12 coupled to sensor body 14. Sensor body 14 includes a metal oxide semiconductor-based toxic gas sensor, such as a hydrogen sulfide gas sensor, which may be a "traditional" metal oxide semiconductor sensor or an NE-MOS based semiconductor gas sensor. Lower portion 16 of sensor body 14 is configured to expose the toxic gas sensor to ambient air in order to determine a concentration of a toxic gas, such as hydrogen sulfide gas, in the ambient air. The sensor within sensor body 14 is coupled to suitable electronics (shown in FIG. 2) within enclosure 12 via conduit 18. Electronics within enclosure 12 can amplify, linearize, and otherwise characterize the sensor response in order to provide an indication of toxic gas concentration. This indication can be provided over a process communication loop or segment, via process wiring through conduit 20, and/or provided locally. A local indication of toxic gas can include a local operator interface (LOI) displaying a toxic gas concentration, an audible or visual alarm, or any combination thereof.

Figure 2:
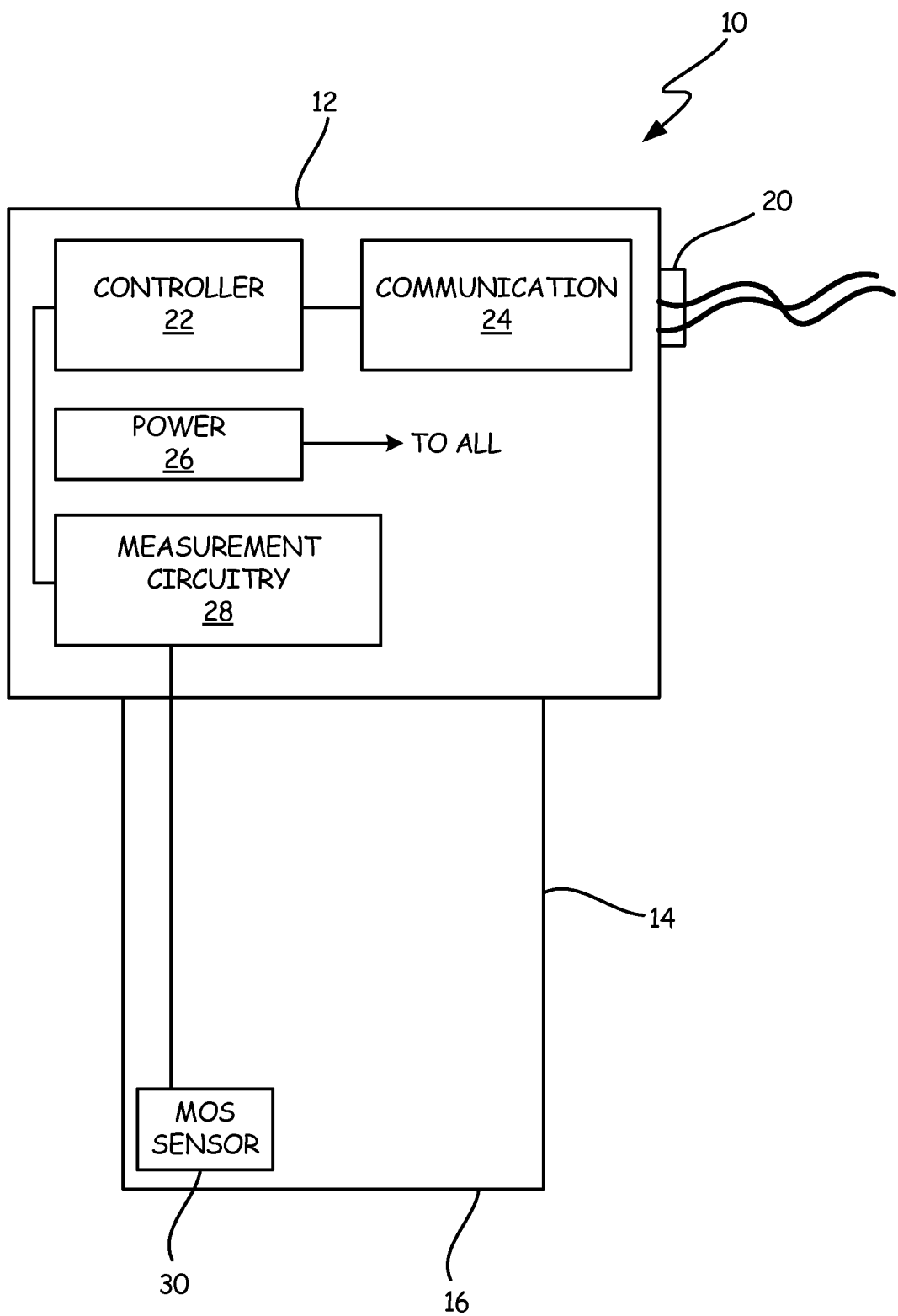
FIG. 2 is a block diagram of a metal oxide semiconductor toxic gas detector in accordance with an embodiment the present invention.

FIG. 2 is a block diagram of a metal oxide semiconductor toxic gas detector in accordance with an embodiment the present invention. Detector 10 includes electronics enclosure 12 coupled to sensor body 14. Disposed within electronics enclosure 12 are controller 22, communication module 24, power module 26, and measurement circuitry 28. Metal oxide semiconductor-based toxic gas sensor 30 is disposed within sensor body 14 and is coupled to measurement circuitry 28.

Controller 22 may be any suitable processing circuitry that is able to apply digital processing techniques or filtering to the sensor measurement in order to determine or otherwise characterize variability or fluctuations in the sensor signal. Additionally, controller 22 is also configured to generate a toxic gas concentration output based on the sensor measurement(s). In one embodiment, controller 22 is a microprocessor. Controller 22 is coupled to communication circuitry 24 to allow controller 22 to communicate with other devices in the process control and monitoring system. Communication circuitry can include circuitry that allows controller 22 to communicate in accordance with a process industry standard communication protocol, such as the Highway Addressable Remote Transducer (HART®) protocol, the FOUNDATION™ Fieldbus protocol, or others. Additionally, in some embodiments, device 10 may communicate wirelessly in addition to or instead of using wired process communication. For example, in one embodiment, communication circuitry 24 may allow communication in accordance with IEC62591. Finally, communication circuitry may provide communication of local outputs, such as a local display or alarm.

Power module 26 is coupled to all components within enclosure 12, as indicated by the arrow labeled "To All." Power module 26 is configured to receive power from a suitable source and provide voltage adjustment or suitable power conditioning to the circuitry within enclosure 12. In some embodiments, power module 26 may be coupled to a wired process communication loop such that device 10 can receive all of its operating energy from the wired process communication loop. In other embodiments, power module 26 may be coupled to a suitable source AC or DC power.

Measurement circuitry 28 is coupled to controller 22 and is able to obtain measurements from semiconductor-based toxic gas sensor 30 and provide digital indications thereof to controller 22. Measurement circuitry 28 may include one or more analog-to-digital converters, suitable multiplexor circuitry, as well as amplification and/or linearization circuitry. Further, measurement circuitry 28 may include suitable filter circuitry, such as a low-pass filter, that is selectively interposable between the sensor and an analog-to-digital converter. In such embodiment, interposing such a low-pass filter between the sensor and an analog-to-digital converter would allow a direct measurement of a signal representative of a toxic gas sensor concentration. Then, bypassing the low pass filter would allow an analog-to-digital converter to measure fluctuations relative to the sensor signal, which fluctuations are indicative of proper sensor functioning. However, it should be noted, that embodiments of the present invention can be practiced where no analog filtering is used, and where both fluctuations and the toxic gas sensor concentration are obtained mathematically from a plurality of analog-to-digital sensor measurements.

Figure 3:
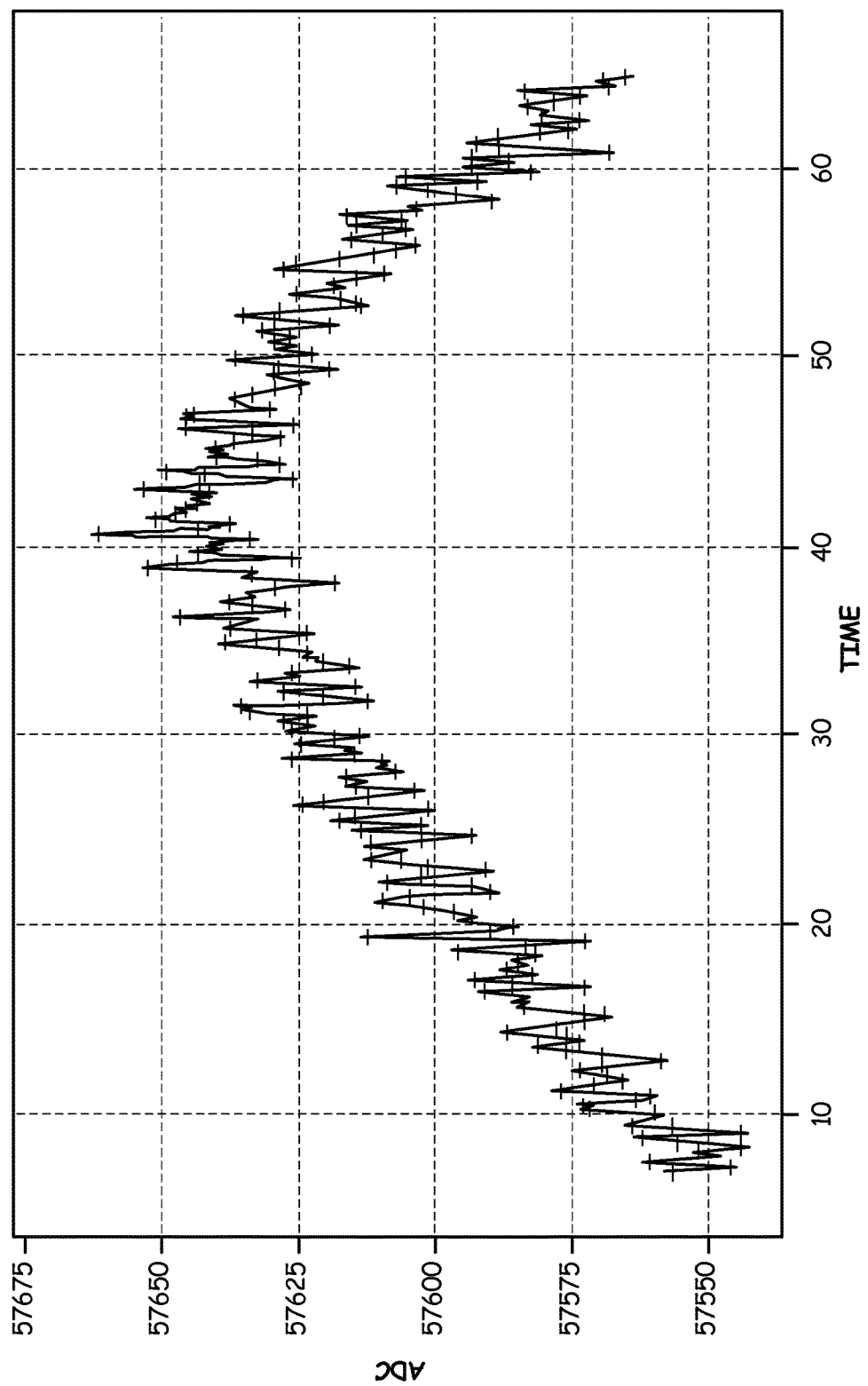
FIG. 3 is a diagrammatic scatter plot of analog-to-digital signal measurements over time for a metal oxide semiconductor toxic gas sensor.

FIG. 3 is a diagrammatic scatter plot of analog-to-digital signal measurements over time for a metal oxide semiconductor toxic gas sensor. As shown in FIG. 3, the sensor exhibits detectable fluctuations or variability. In the example shown in FIG. 3, the toxic gas concentration is shown varying from a time of approximately five minutes to a time of approximately 70 minutes. The vertical axis is an analog-to-digital converter count for each individual measurement. The toxic gas concentration varies with a gradual increase from a time of 5 minutes to time of 40 minutes when the sensor has an output of approximately 57,850 counts. At time a time of about 40, the toxic gas concentration begins to diminish gradually until at approximately time T=65 minutes, when the analog-to-digital count is approximately 57,775. As shown in the example, the variability is typically on the order of approximately 25 counts. In accordance with various embodiments of the present invention, while the toxic gas concentration may be processed in any suitable manner to remove effects of variation or otherwise average values over a short window of time in order to provide a relatively stable toxic gas concentration output, a diagnostic output is generated based substantially on the fluctuations. The fluctuations may be detected or otherwise observed in any suitable manner. For example, an array or other suitable memory structure may be filled with a sequence of analog-to-digital converter measurements over a fixed period of time, or simply a certain number of measurements. The memory structure may be updated such that when a new measurement is obtained, the oldest measurement is discarded. Controller 22, or any other suitable processor, may operate digitally upon the stored array or sequence of measurements in order to obtain information about fluctuation characteristics, such as variability. For example, the variance of the set of measurements may simply be calculated in accordance with known statistical techniques. However, any other suitable mathematic operations that can provide useful information regarding the degree of fluctuation can be used in accordance of the embodiments of the present invention.

Figure 4:
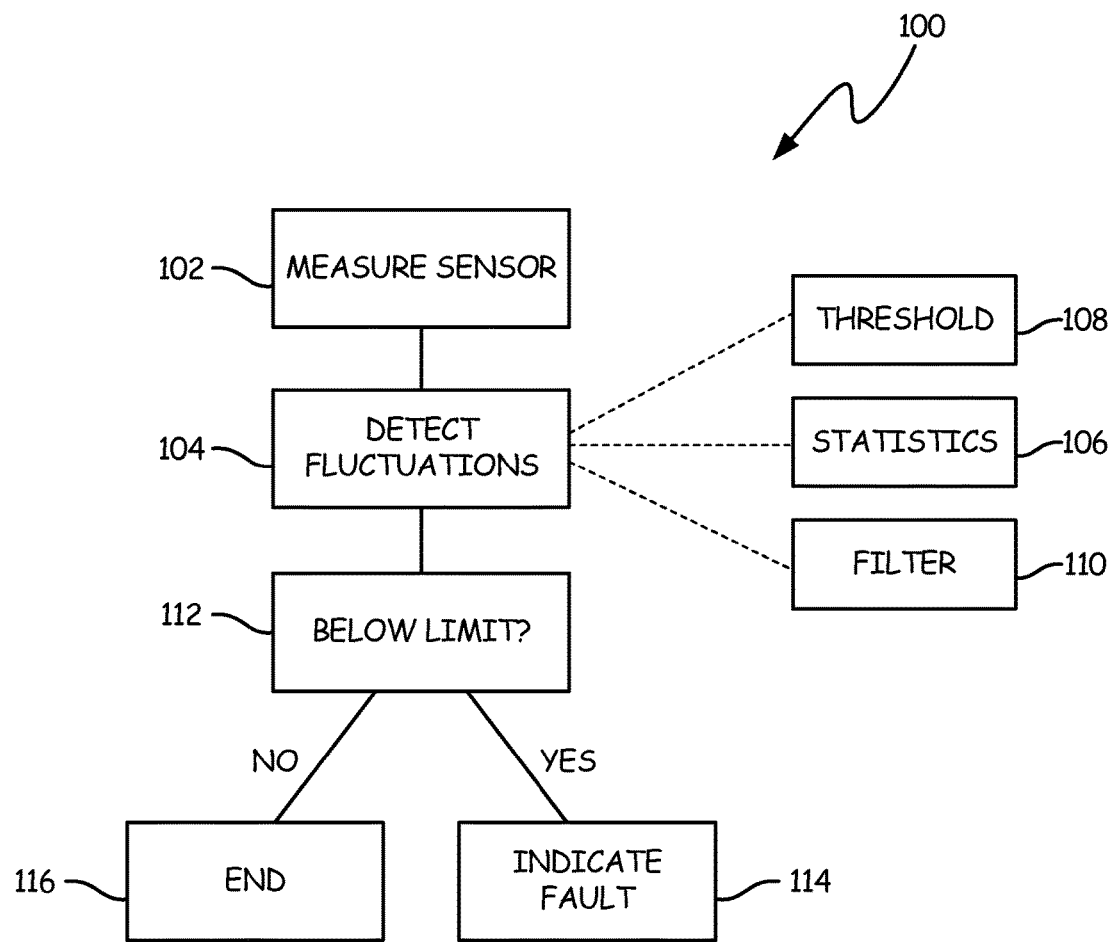
FIG. 4 is a flow diagram of a method of generating a diagnostic indication relative to a semiconductor metal oxide toxic gas sensor in accordance with an embodiment of the present invention.

FIG. 4 is a flow diagram of a method of generating a diagnostic indication relative to a semiconductor metal oxide toxic gas sensor in accordance with an embodiment of the present invention. Method 100 begins at block 102 where a plurality of sensor measurements are obtained. These sensor measurements are obtained over a suitable period of time, for example, a span of several seconds or even minutes. Next, at block 104, fluctuations in the sensor signal measurements are detected. As set forth above, in one embodiment, a number of sensor measurements may be stored in memory and processed in accordance with any suitable mathematic techniques in order to detect variability. For example, statistical processing techniques 106 can be used to detect such fluctuations. Additionally, or alternatively, the differences between individual measurements can be processed or otherwise subjected to a threshold process 108. Finally, the stored measurements may be subjected to a digital filter 110 in order to amplify or otherwise highlight variability in the sensor signal measurements. Next, at block 112, the detected fluctuations or variability is compared to a preselected limit. This limit may be defined or otherwise set during manufacture of the device or it may be set during commissioning of the device. For example, one particular toxic gas sensor may exhibit more variability than another type of toxic gas sensor. Thus, when the detector is commissioned with a specific toxic gas sensor, a variability threshold suitable for that sensor can be set. If the detected variability of the semiconductor based toxic gas sensor is below the selected limit, control passes to block 114 where controller 22 will generate a diagnostic indication. This diagnostic indication may be the generation of a fault or error message that is conveyed over a process communication loop or segment, a local indication indicated visually or audibly at the detector, or any combination thereof. Alternatively, if the detected variability is not below the selected limit, control passes to block 116 and method 100 ends. Accordingly, the detector will simply provide a toxic gas concentration output without providing any indication of fault.

Method 100 can be executed periodically, such as once a minute, or in response to any suitable input signal. For example, a technician may press a button or otherwise send a command to device 10 causing device 10 to execute method 100. Additionally, the frequency with which method 100 is executed can also be a function of the toxic gas sensor concentration value. For example, if device 10 is indicating a toxic gas sensor concentration above a selected threshold, method 100 can execute with a first frequency, while if the toxic gas sensor concentration is below the selected threshold, method 100 can execute with a different frequency.

It is believed that embodiments of the present invention will provide important diagnostics for metal oxide semiconductor-based toxic gas sensors by detecting when a sensor signal is stale. This will allow remedial action to be taken before the sensor deteriorates further and either opens or shorts. Further still, embodiments of the present invention are able to detect when an otherwise functioning metal oxide-based semiconductor toxic gas sensor (e.g. neither open nor shorted) is nonetheless failing to accurately indicate toxic gas concentration.

Although the present invention has been described with reference to preferred embodiments, workers skilled in the art will recognize that changes may be made in form and detail without departing from the spirit and scope of the invention.

What is claimed is:

1. A metal oxide semiconductor-based toxic gas detector comprising:
    a metal oxide semiconductor-based gas sensor, the gas sensor having an electrical characteristic that varies with a concentration of a toxic gas;
    measurement circuitry coupled to the metal oxide semiconductor-based gas sensor, the measurement circuitry being configured to measure the electrical characteristic and provide a digital indication of the measured electrical characteristic; and
    a controller coupled to the measurement circuitry and configured to provide a toxic gas output based on the digital indication, the controller being further configured to detect a fluctuation in measured digital indications of the measured electrical characteristic over a period of time, and, based on the detected fluctuation, provide a diagnostic indication relative to the metal oxide semiconductor-based sensor.

2. The metal oxide semiconductor-based toxic gas detector of claim 1, and further comprising communication circuitry coupled to the controller and configured to communicate in accordance with a process industry standard communication protocol.

3. The metal oxide semiconductor-based toxic gas detector of claim 2, wherein the communication circuitry is wireless communication circuitry.

4. The metal oxide semiconductor-based toxic gas detector of claim 1, wherein the controller is coupled to memory that stores a plurality of digital indications and wherein the controller processes the plurality of digital indications in order to determine a level of fluctuations.

5. The metal oxide semiconductor-based toxic gas detector of claim 4, wherein the processing includes determining a statistical quantity relative to the plurality of digital indications.

6. The metal oxide semiconductor-based toxic gas detector of claim 5, wherein the statistical quantity is a fluctuation characteristic obtained digitally.

7. The metal oxide semiconductor-based toxic gas detector of claim 4, wherein the level of fluctuations is compared to a pre-determined threshold in order to generate the diagnostic indication.

8. The metal oxide semiconductor-based toxic gas detector of claim 7, wherein the threshold is related to a type of the metal oxide semiconductor-based toxic gas sensor.

9. The metal oxide semiconductor-based toxic gas detector of claim 7, wherein the diagnostic indication is communicated over a process communication loop or segment.

10. The metal oxide semiconductor-based toxic gas detector of claim 7, wherein the diagnostic indication is provided locally by the detector.

11. A method of operating a toxic gas detector having a metal oxide semiconductor-based toxic gas sensor, the method comprising;
    obtaining a sequence of measurements of an electrical characteristic of the metal oxide semiconductor-based toxic gas sensor;
    processing, using a controller of the toxic gas detector, the sequence of measurements of electrical characteristics to detect a fluctuation in the measurements:
    providing a toxic gas detector output based on at least one of the electrical characteristic measurements; and
    generating a diagnostic output based on the detected fluctuations, and wherein diagnostic indication comprises a detected stale sensor.

12. The method of claim 11, wherein generating the diagnostic output based on the fluctuations includes calculating a statistical quantity of the sequence of measurements.

13. The method of claim 12, wherein the statistical quantity is indicative of a fluctuation characteristic obtained digitally.

14. The method of claim 12, wherein the statistical quantity is compared to a pre-determined threshold in order to determine whether to generate the diagnostic output.

15. The method of claim 11, wherein the diagnostic output is communicated over a process communication loop or segment.

16. The method of claim 11, wherein the diagnostic output is communicated wirelessly.

17. The method of claim 11, wherein the diagnostic output is communicated locally by the toxic gas detector.

* * * * *